United States Patent [19]

Miles

[11] Patent Number: 5,427,794
[45] Date of Patent: Jun. 27, 1995

[54] INSECTICIDAL COMPOSITION AND INSECTICIDAL UNITS

[75] Inventor: David L. Miles, Chapel Hill, N.C.

[73] Assignee: Rhone-Poulenc AG Company, Research Triangle Park, N.C.

[21] Appl. No.: 111,035

[22] Filed: Aug. 24, 1993

Related U.S. Application Data

[63] Continuation of Ser. No. 858,523, Mar. 27, 1992, abandoned, which is a continuation-in-part of Ser. No. 680,301, Apr. 4, 1991, abandoned, Ser. No. 679,290, Apr. 2, 1991, abandoned, and Ser. No. 713,684, Jun. 11, 1991, abandoned.

[51] Int. Cl.$^6$ ............................................. A01N 25/00
[52] U.S. Cl. ..................................... 424/405; 424/400
[58] Field of Search ................. 424/401, 405; 514/521

[56] References Cited

U.S. PATENT DOCUMENTS

| | | | |
|---|---|---|---|
| 3,277,009 | 10/1966 | Friefield | 252/96 |
| 4,310,520 | 1/1982 | Narazaki | 424/200 |
| 4,310,520 | 1/1982 | Narozaki | 514/531 |
| 4,325,969 | 4/1982 | Brown | 514/521 |
| 4,416,791 | 11/1987 | Hoq | 252/96 |
| 5,137,653 | 8/1991 | Pawson | 424/405 |
| 5,178,871 | 1/1993 | Thill | 424/405 |

FOREIGN PATENT DOCUMENTS 0190776 8/1986 European Pat. Off. .
0251464 7/1988 European Pat. Off. .

*Primary Examiner*—Thurman K. Page
*Assistant Examiner*—Peter F. Kulkosky

[57] ABSTRACT

A non-aqueous insecticidal unit comprising an insecticidal composition concentrate in the form of a water soluble or water dispersible gel contained in a cold water soluble or dispersible bag. The bag upon being solubilized or dispersed in water is capable of being used in an agricultural chemical spray unit. The composition comprises a synthetic pyrethroid, a solvent, at least one gelling agent, at least one emulsifier, at least one antifoaming agent, at least one antioxidant and an acidic agent.

1 Claim, No Drawings

INSECTICIDAL COMPOSITION AND INSECTICIDAL UNITS

This is a continuation of application Ser. No. 07/858,523, filed on Mar. 27, 1992, now abandoned, which is a continuation-in-part of U.S. Ser. No. 680,301, filed on Apr. 4, 1991, and now abandoned, U.S. Ser. No. 679,290, filed on Apr. 2, 1991, and now abandoned, and U.S. Ser. No. 713,684, filed on Jun. 11, 1991, and now abandoned.

BACKGROUND OF THE INVENTION

I. Field of the Invention

The invention relates to insecticidal compositions and to insecticidal units which are particularly suitable for storing, packaging and transporting insecticidal concentrates of pyrethroids.

II. Discussion of the Prior Art

There are many difficulties in producing the optimum formulation of any given active ingredient. The first requirement of any formulation is chemical stability. However, safety must come high on the list of important attributes. This can include worker exposure, safety for the environment, including spills, and container disposal issues. Most agricultural chemicals are diluted in water before spraying and need to be easily dispersible in water of various hardnesses and pH. Formulations need to be physically stable and this includes seperation or breakdown of the product which affects any of the other properties.

Other properties desirable for formulations include the ability to withstand low temperatures without affecting loading or causing crystallization. The formulations must be useable without excess foaming, be compatible with other commonly used pesticides, and at the same time maintain the best biological activity. Bags have been also used for containing pesticidal compositions, but this renders the problem still more complicated due to the fact that the bags should be compatible with their contents.

An object of the instant invention is to provide an insecticidal composition and insecticidal unit having most or all of these properties.

An object of the instant invention is to provide an insecticidal composition and insecticidal unit containing pyrethroid as active ingredient and having most or all of these properties.

SUMMARY OF THE INVENTION

The insecticidal unit according to the invention comprise an insecticidal composition (which is itself part of the invention) contained in a water soluble bag, the said composition comprising a synthetic pyrethroid, and a solvent if the pyrethroid is solid at room temperature, and at least one gelling agent, and at least one emulsifier, and at least one antifoaming agent, and optionally at least one antioxidant, and optionally an acidic agent.

Another feature of the instant invention is an insecticidal composition and insecticidal unit wherein the said composition has a water dispersibility such as its spontaneity (as hereafter defined) less than 20, preferably less than 10.

Another feature of the instant invention is an insecticidal composition and insecticidal unit having practically no flowing through pinholes and such as its tg(phi) (as hereafter defined) is less than 1, preferably less than 0.5.

Another feature of the instant invention is an insecticidal composition and insecticidal unit wherein the complex viscosity (as hereafter defined) is higher than 20 Pa.s at 10 rd/s and less than 1000 Pa.s at 1 rd/s.

Another feature of the instant invention is an insecticidal composition and insecticidal unit wherein the storage modulus (G' measured as hereafter defined, under speed of oscillations of 1 rd/s=radian per seconde) is in the range of 1 to 10000 Pascal, preferably 10 to 5000 Pascal.

DETAILED DESCRIPTION OF THE INVENTION

Many kind of pyrethroids may be used in the invention, such as permethrin, cypermethrin, cyfluthrin, lambda cyhalothrin. The pyrethroids which are most preferred in the invention are deltamethrin or tralomethrin; in the compositions comprising one of these two pyrethroids, the antioxidant and the acidic agent are included in the compositions of the invention.

Solvents which can be used in the invention are preferably liquid at room temperature. The solvent in the invention may be a single solvent or mixture of solvents. They may be, for example, selected in the group comprising the liquid alkyl substituted aromatic hydrocarbons; the ketones having from 6 to 12 carbon atoms in their molecula; butyrolactone; N-alkyl pyrrolidone, especially N-methyl-, N-octyl-, N-decyl- and N-cyclohexyl-pyrrolidone; saturated or unsaturated aliphatic acids having from 6 to 18 carbon atoms in their molecula; aliphatic or aromatic aldehydes having from 6 to 24 atoms in their molecula; the salicylic acid; the anthranilic acid; the alkyl or alkenyl esters of such aliphatic or of aromatic acids, such as benzoates, salicylates or anthranilates, especially esters having 1 to 8 carbon atoms in the alcoholic part of the ester molecula; the alkyl or aryl ethers; the aliphatic or aromatic or heterocyclic substituted alcohols; the lactones; the amides.

Preferred solvents are alkyl aromatic hydrocarbons having 10 to 16 carbon atoms; methyl esters of alkanoic and alkenoic acids having 8 to 18 carbon atoms; esters mixtures derivated from plant oils, generally methyl esters of saturated or insaturated acids having 8 to 18 carbon atoms; methyl salicylate; N methyl pyrrolidone; tetrahydrofuran; butyrolactone; tetrahydrofurfuryl alcohol and esters thereof; and mixtures thereof.

Emulsifiers which can be used in the invention may be of any type, anionic or non-ionic or cationic or ampothoteric surfactants. More preferably these emulsifiers are chosen so that their HLB (=hydrophilic lipophilic balance; this HLB is known in the art and tables are published giving the HLB for solvents which can be used) is close to the HLB of the solvent; preferably the difference is not greater than 2. The HLB of the emulsifier which is considered herein is the global HLB of all the surface active agent in the formulation. Among all these emulsifiers, the mixtures anionic+non ionic are advantagous.

Specific emulsifiers which are advantageous in the compositions of the invention are: dialkyl sulfosuccinates; alkylbenzene sulfonates salts, such as calcium dodecyl benzene sulfonate; ethoxylated tristyryl phenols, and sulfates and phosphates thereof; alkyl poylethoxyether phosphates esters, either in acid or in salt form; ethoxylated fatty acids or alcohols; ethoxylated alkyl phenols or dialkyl phenols; ethoxylated castor oil; ethoxylated propoxylated block copolymers; ethoxylated propoxylated alkylphenol block copolymers; ethoxylated propoxylated tristyrylphenols; glycerol esters, especially esters of fatty acids; glycol esters, especially esters of fatty acids; lecithin and lecithin derivatives; sugar esters and other derivatives, as sorbitol, and sucrose or glucose esters or derivatives; sucroglycerides.

Gelling agents which can be used in the invention are generally solid and of low solubility in the liquid system (either the pyrethroid alone or the mixture pyrethroid+solvent) and able to form a homogeneous mixture as can be seen visually with the emulsifier of the insecticidal composition. Furthermore, the gelling agent is preferably also able to form a homogeneous, as can be seen visually, ternary mixture with the solvent and the emulsifier. It happens sometimes that the gelling agents are mixtures of different compounds which might not be gelling agents alone.

Gelling agents which can be advantageously used are: polyacrylic derivatives such as polyacrylic salts, especially the alkali or ammonium salts; sodium dioctyl sulfosuccinate, optionally mixed with organic salts, such as sodium benzoate; silica; sodium acetate in combination with other compounds; urea; alumina; titanium dioxide; sugars; lignosulfonates; salts of alkyl arylsulfonates, such as sodium dodecyl benzene sulfonate; combinations of modified clay and propylene carbonate; hydrogenated castor oil; ethoxylated vegetable oil; tetramethyl decynediol; mixtures of dimethyl hexane diol and hexyne diol; and mixtures thereof. Some gelling agents might have both an emulsifying action and a gelling action such as ethoxylated/propoxylated alkyl phenol block copolymers; ethoxylated alkyl phenols and dialkyl phenols; ethoxylated fatty acids; ethoxylated fatty alcohols; ethoxylated propoxylated block copolymers; and mixtures thereof.

Antifoaming which can be used in the invention are compounds which are known to be antifoaming per se. Preferably they are a poly dialkylsiloxane as polydimethyl siloxane or a hydrocarbon oil or tetramethyldecynediol and dimethyl octynediol. They may have both antifoaming and surface-active properties, such as tetramethyldecynediol.

Antioxidants which can be used in the invention are generally of the phenolic type, such as alkyl phenols, alkyl gallates, ascorbic acid and tocopherol. More specifically, preferred antioxidants in the invention are butylated hydroxy toluene or anisol.

As already said, the insecticidal unit in the invention comprise also an acidic agent. This agent is preferably selected in the group comprising aliphatic saturated or unsaturated acids, especially acetic acid; phosphoric acid or acidic salts; sulfuric acid; hydrochloric acid; acidic surfactant named above.

The gel material which is used in the invention is essentially a material which has a phase difference phi between the controlled shear stress and the resulting shear strain such that tg(phi) is less than or equal to 1, preferably less than or equal to 0.5. Tg(phi) is the tangent of the phi angle (or phase difference). The measurement of phi is made by means of a dynamic rheometer. Dynamic rheometers which are appropriate to measure phi are known and available commercially. They usually have a flat fixed plate and a rotating cone or plate, or a so-called couette measuring system. Other mechanical systems are also available. Generally the choice of one system or another is made according to the recommandations of the seller of the rheometer, and is adopted to the kind of compound, gel or liquid, which is tested. The particular choice of a specific type of rheometer is something well known by the man skilled in the art of rheology. A rotating plate over another plate or a cone rotating over a plate are often more appropriate when a gel or a viscous liquid is tested. When two kinds of system for the rheometer are possible, similar values of phi are actually measured. The cone (or the plate or the couette) is caused to rotate by means of a controlled speed motor; the rotation is a sinusoidal one, i.e., the strain and the angular displacement change as a sine function with time. Tg(phi) is equal to the ratio $G''/G'$, wherein: $G'$ is the storage modulus (represents the behaviour of a perfect solid); $G''$ is the loss modulus (represents the behaviour of a perfect liquid). $G'$ and $G''$ are expressed in Pascal for a given rotational speed (radian per second).

$G'$ and $G''$, and thus tg(phi), may depend on the amplitude of the oscillations (percentage of strain) of the rheometer; however, there is generally a so-called viscoelastic plateau whereby the values $G'$ and $G''$ of a gel do not depend substantially on the said amplitude; this means that in the conditions of the test under the viscoelastic plateau the structure of the gel is maintained and no destruction of the gel into a liquid happens. Of course, the measurement of $G'$ and $G''$ of a gel is made under the conditions of this viscoelastic plateau, just because it corresponds to the normal gel structure which is precisely what is tested.

$G'$ and $G''$, and thus tg(phi), may also depend on the speed of the oscillations (time to reach the chosen percentage of strain; expressed as radian per seconde) of the rheometer; however, when the gel is well structured, there is no so much variation from one speed to another. In order to have a reasonable measurement of the properties of a gel, it is generally preferred to operate in conditions whereby the gel is not too much stressed, that is to say at speed such as 1 rd/s. Of course, measurements at higher speed may also be made.

The insecticidal unit of the instant invention comprise an insecticidal composition in a bag. This bag is generally made of a polymeric material in form of a film, and this film constitutes the wall of the bag. Polymeric material which can be used in the invention are polyvinylalcohol; cellulosic materials such as methyl or ethyl cellulose; poly alkylene oxides. A preferred material is the polyvinylalcohol, which is advantageously totally or partially hydrolyzed or alcoholyzed polyvinylacetate. The hydrolysis or alcoholysis rate of polyvinyl acetate in the invention is generally between 70 to 90%. All these materials should be cold water soluble (cold means, here, less than 35° C.).

As already said, the insecticidal unit comprise an insecticidal composition contained in a water soluble bag, the said composition comprising a synthetic pyrethroid and a solvent and at least one gelling agent and at least one emulsifier and at least one antifoaming agent and at least one antioxidant and an acidic agent.

The volume of the bag is generally comprised between 40 ml and 5 liters, preferably between 0.1 and 3 liters.

The amount of pyrethroid in the insecticidal composition of the invention is generally comprised between 0.5 and 60% of the total insecticidal composition contained in the bag, preferably between 1 and 40% (in the present specification, unless otherwise specified, the percentage are w/w); for deltamethrin and tralomethrin an amount of 1 to 20% is preferred.

The amount of emulsifier in the insecticidal composition of the invention is generally comprised between 2 and 30% of the total insecticidal composition contained in the bag, preferably between 4 and 20%.

The amount of gelling agent in the insecticidal composition of the invention is generally comprised between 0.5 and 20% of the total insecticidal composition contained in the bag, preferably between 0.8 and 10%.

The amount of antifoaming agent in the insecticidal composition of the invention is generally comprised between 0.05 and 5% of the total insecticidal composition contained in the bag, preferably between 0.1 and 0.5%.

The amount of antioxidant in the insecticidal composition of the invention is generally comprised between 0.01 and 1% of the total insecticidal composition contained in the bag, preferably between 0.5 and 0.2%.

The amount of acidic agent in the insecticidal composition of the invention is generally comprised between 0.01 and 1% of the total insecticidal composition contained in the bag, preferably between 0.05 and 0.5%.

A particular embodiment of the present invention is an insecticidal unit comprising an insecticidal composition contained in a water soluble bag, the said composition comprising a synthetic pyrethroid and a solvent and at least one gelling agent and at least one emulsifier and at least one antifoaming agent and at least one antioxidant and an acidic agent.

Another particular embodiment of the present invention is an insecticidal unit comprising an insecticidal composition contained in a water soluble bag, the said composition comprising deltamethrin or tralomethrin and a solvent and at least one gelling agent and at least one emulsifier and at least one antifoaming agent and at least one antioxidant and an acidic agent.

Another particular embodiment of the present invention is an insecticidal unit comprising an insecticidal composition contained in a water soluble bag, the said composition comprising a synthetic pyrethroid and a solvent and at least one gelling agent and at least one emulsifier and at least one antifoaming agent and at least one antioxidant and an acidic agent, and the said composition having tg(phi) less than 1.

Another particular embodiment of the present invention is an insecticidal unit comprising an insecticidal composition contained in a water soluble bag, the said composition comprising a synthetic pyrethroid and a solvent and at least one gelling agent and at least one emulsifier and at least one antifoaming agent and at least one antioxidant and an acidic agent, and the said composition having tg(phi) less than 0.5.

Another particular embodiment of the present invention is an insecticidal unit comprising an insecticidal composition contained in a water soluble bag, the said composition comprising a synthetic pyrethroid and a solvent and at least one gelling agent and at least one emulsifier and at least one antifoaming agent and at least one antioxidant and an acidic agent, and the said composition having a complex viscosity higher than 20 Pa.s at 10 rd/s and less than 1000 Pa.s at 1 rd/s and/or a storage modulus in the range of 1 to 10000 Pascal, preferably 10 to 5000 Pascal.

Another particular embodiment of the present invention is an insecticidal unit comprising an insecticidal composition contained in a water soluble bag, the said composition comprising a synthetic pyrethroid and a solvent and at least one gelling agent and at least one emulsifier and at least one antifoaming agent and at least one antioxidant and an acidic agent, and the said composition having a spontaneity less than 20.

Another particular embodiment of the present invention is an insecticidal unit comprising an insecticidal composition contained in a water soluble bag, the said composition comprising a synthetic pyrethroid and a solvent and at least one gelling agent and at least one emulsifier and at least one antifoaming agent and at least one antioxidant and an acidic agent, and the said composition having a spontaneity less than 10.

Another particular embodiment of the present invention is an insecticidal unit according to any one of previous embodiments wherein the water soluble bag is made of polyvinylalcohol film.

Another particular embodiment of the present invention is an insecticidal unit according to any one of previous embodiments wherein the water soluble bag is made of partially hydrolized polyvinyl acetate having an hydrolysis rate between 70 and 90%.

Another particular embodiment of the present invention is an insecticidal unit according to any one of previous embodiments wherein the solvent is a liquid at room temperature selected in the group comprising the aromatic, optionally alkyl substituted, hydrocarbons; the ketones having from 6 to 12 carbon atoms in their molecula; the butyrolactone; the N-methyl pyrrolidone; the alkanoic acids having from 6 to 12 carbon atoms in their molecula; the aliphatic or aromatic aldehyde having from 6 to 24 carbon atomes in their molecula; the salicylic acid; the anthranilic acid; the alkyl or alkenyl esters of such alkanoic or salicylic or anthranilic acids having 1 to 5 carbon atoms in the alcoholic part of the ester molecula; the alkyl or aryl ethers; the aliphatic or aromatic alcohols; the lactones; the amides.

Another particular embodiment of the present invention is an insecticidal unit according to any one of previous embodiments wherein the gelling agent is a solid which is insoluble in the solvent and miscible with the emulsifier of the insecticidal composition.

Another particular embodiment of the present invention is an insecticidal unit according to any one of previous embodiments wherein the gelling agent is a solid which is insoluble in the solvent and miscible with the emulsifier of the insecticidal composition and able to form a homogeneous tenary mixture with the solvent and the emulsifier.

Another particular embodiment of the present invention is an insecticidal unit according to any one of previous embodiments wherein the insecticidal composition is in the form of an emulsion wherein the average size of the droplets is less than 10 microns.

Another particular embodiment of the present invention is an insecticidal unit according to any one of previous embodiments wherein the insecticidal composition is in the form of an emulsion wherein the average size of the droplets is less than 3 microns.

Another particular embodiment of the present invention is an insecticidal unit according to any one of previous embodiments wherein the emulsifier or the emulsifiers are anionic or non-ionic or cationic or amphoteric surfactants where HLB matches said system and emulsion of less than 10 microns are observed, preferably where emulsions of less than 3 microns are observed.

Another particular embodiment of the present invention is an insecticidal unit according to any one of previous embodiments wherein the antioxidant is of the phenolic type.

Another particular embodiment of the present invention is an insecticidal unit according to any one of previous embodiments wherein the antioxidant is selected in the group consisting of butylated hydroxytoluene and butylated hydroxyanisol Another particular embodiment of the present invention is an insecticidal unit according to any one of previous embodiment wherein the acidic agent is selected in the group comprising acetic acid, phosphoric acid, sulfuric acid, hydrochloric acid, phosphonic surfactants.

Another particular embodiment of the present invention is an insecticidal composition comprising a synthetic pyrethroid and a solvent and at least one gelling agent and at least one emulsifier and at least one antifoaming agent and at least one antioxidant and an acidic agent.

Another particular embodiment of the present invention is an insecticidal composition comprising deltamethrin or tralomethrin and a solvent and at least one gelling agent and at least one emulsifier and at least one antifoaming agent and at least one antioxidant and an acidic agent.

Another particular embodiment of the present invention is an insecticidal composition according to any one of previous embodiment wherein the water soluble bag is made of polyvinylalcohol film.

Another particular embodiment of the present invention is an insecticidal composition according to any one of previous embodiment wherein the water soluble bag is made of partially hydrolized polyvinyl acetate having an hydrolysis rate between 70 and 90%.

Another particular embodiment of the present invention is an insecticidal composition according to any one of previous embodiment wherein the solvent is a liquid at room temperature selected in the group comprising the aromatic, optionally alkyl substituted, hydrocarbons; the ketones having from 6 to 12 carbon atoms in their molecula; the butyrolactone; the N-methyl pyrrolidone; the alkanoic acids having from 6 to 12 carbon atoms in their molecula; the aliphatic or aromatic aldehyde having from 6 to 24 carbon atomes in their molecula; the salicylic acid; the anthranilic acid; the alkyl or alkenyl esters of such alkanoic or salicylic or anthranilic acids having 1 to 5 carbon atoms in the alcoholic part of the ester molecula; the alkyl or aryl ethers; the aliphatic or aromatic alcohols; the lactones; the amides.

Another particular embodiment of the present invention is an insecticidal composition according to any one of previous embodiment wherein the gelling agent is a solid which is insoluble in the solvent and miscible with the emulsifier of the insecticidal composition.

Another particular embodiment of the present invention is an insecticidal composition according to any one of previous embodiment wherein the gelling agent is a solid which is insoluble in the solvent and miscible with the emulsifier of the insecticidal composition and able to form a homogeneous ternary mixture with the solvent and the emulsifier.

Another particular embodiment of the present invention is an insecticidal composition according to any one of previous embodiment wherein the insecticidal composition is in the form of an emulsion wherein the average size of the droplets is less than 10 microns.

Another particular embodiment of the present invention is an insecticidal composition according to any one of previous embodiment wherein the insecticidal composition is in the form of an emulsion wherein the average size of the droplets is less than 3 microns.

Another particular embodiment of the present invention is an insecticidal composition according to any one of previous embodiment wherein the emulsifier or the emulsifiers are anionic or non-ionic or cationic or amphoteric surfactants where HLB matches said system and emulsion of less than 10 microns are observed, preferably where emulsions of less than 3 microns are observed.

Another particular embodiment of the present invention is an insecticidal composition according to any one of previous embodiment wherein the antioxidant is of the phenolic type.

Another particular embodiment of the present invention is an insecticidal composition according to any one of previous embodiment wherein the antioxidant is selected in the group consisting of butylated hydroxytoluene and butylated hydroxyanisol.

Another particular embodiment of the present invention is an insecticidal composition according to any one of previous embodiment wherein the acidic agent is selected in the group comprising acetic acid, phosphoric acid, sulfuric acid, hydrochloric acid, phosphonic surfactants.

The following examples are given to illustrate the inventions and some mode of realisation. It is not intended to restrict the invention to these particular examples.

EXAMPLE 1

A first composition is made by stirring a mixture of

| | |
|---|---|
| Deltamethrin | 2.5% |
| Alkyl aromatic hydrocarbon (flash point is 93° C.) | 84.2% |
| Sodium lauryl sulfate (gelling) | 3.3% |
| sodium dioctyl sulfosuccinate + sodium benzoate (gelling and emulsifying agent) | 2% |
| ethoxylated propoxylated alkyl benzene (gelling and emulsifying) | 3.5% |
| calcium dodecyl benzene sulfonate (emulsifying agent) | 3.5% |
| dimethyl polysiloxane (antifoaming agent) | 0.5% |
| ethoxylated alkyl phosphate ester (acid and emulsifying agent) | 0.5% |

EXAMPLE 2

A second composition is made by stirring a mixture of

| | |
|---|---|
| Deltamethrin | 2.5% |
| Alkyl aromatic hydrocarbon (flash point is 93° C.) | 84.2% |
| Sodium lauryl sulfate (gelling) | 3.3% |
| sodium alkyl naphtalene sulfonate (gelling agent) | 2% |
| ethoxylated propoxylated alkyl benzene (gelling and emulsifying) | 3.5% |
| calcium dodecyl benzene sulfonate (emulsifying agent) | 3.5% |
| dimethyl polysiloxane (antifoaming agent) | 0.5% |
| ethoxylated alkyl phosphate ester (acid and emulsifying agent) | 0.5% |

The compositions hereabove were filled in bag made of polyvinylalcohol. The volume of the composition was 100 ml, and the volume of the bag was 150 ml. The bags were closed by heat sealing.

Following tests have been performed:

a) The characteristics of the gels were measured as previously indicated.

The insecticidal units of the instant invention are better when the compositions contained therein have the lowest possible tangent: this tangent is correlated with non flowing properties through pinholes at rest.

b) The spontaneity is assessed according to the following method: A mixture of 1 ml gel with 99 ml water are put into a 150 ml glass tube (diameter 22 mm) which is stoppered and inverted by 180 degrees (upside down). The number of inversions required to completely disperse the gel is called the spontaneity.

The insecticidal units of the instant invention are better when the compositions contained therein have the highest possible spontaneity: this spontaneity is correlated with water dispersibility.

c) Stability of gels at different temperatures:

The properties of gels in a bag have been measured after (independent tests)

two weeks at +54° C., two weeks at +4° C.

one cycle of one day at −5° C. followed by one day at +45° C.

Following results have been obtained:

| Formulation of example: | tg(phi) | spontaneity | G' storage modulus |
|---|---|---|---|
| 1 | 0.1 (1 rd/s) | less than 4 | 152 at 1 rd/s (171 at 10 rd/s) |
| 2 | 0.16 (1 rd/s) | less than 4 | 544 at 1 rd/s (633 at 10 rd/s) |

Effect of temperature:

Syneresis was only 2% at 54° C. but the properties of the gel did not substantially vary. The compositions were completely stable for the other tests.

What is claimed is:

1. A non-aqueous insecticidal unit consisting essentially of an insecticidal composition concentrate in the form of a water soluble or water dispersible gel contained in a cold polyvinyl alcohol water soluble or dispersible bag, said bag upon being solubilized or dispersed in water being capable of being used in an agricultural chemical spray unit and said composition comprising a synthetic pyrethroid, a solvent, at least one gelling agent, at least one emulsifier, at least one antifoaming agent, at least one antioxidant and an acidic agent wherein the gel has a tg(phi) of less than 1; a complex viscosity of between 20 Pa.s. at 10 rd/s and less than 1,000 Pa.s. at 1 rd/S; and a storage modulus of between 1 and 10,000 Pascal.

* * * * *